United States Patent
McPherson Allnutt et al.

(10) Patent No.: US 10,493,217 B2
(45) Date of Patent: Dec. 3, 2019

(54) INHALATOR AND INHALATOR SET

(71) Applicant: PARI Pharma GmbH, Starnberg (DE)

(72) Inventors: Tom McPherson Allnutt, Oslo (NO);
Wolfgang Achtzehner, Alling (DE);
Thomas Gallem, München (DE); Uwe Hetzer, München (DE)

(73) Assignee: PARI Pharma GmbH, Starnberg (DE)

( * ) Notice: Subject to any disclaimer, the term of this patent is extended or adjusted under 35 U.S.C. 154(b) by 559 days.

(21) Appl. No.: 15/118,986

(22) PCT Filed: Feb. 25, 2015

(86) PCT No.: PCT/EP2015/053930
§ 371 (c)(1),
(2) Date: Aug. 15, 2016

(87) PCT Pub. No.: WO2015/128375
PCT Pub. Date: Sep. 3, 2015

(65) Prior Publication Data
US 2016/0354557 A1 Dec. 8, 2016

(30) Foreign Application Priority Data
Feb. 25, 2014 (EP) .................................... 14156519

(51) Int. Cl.
*A61M 11/00* (2006.01)
*A61M 15/00* (2006.01)
(Continued)

(52) U.S. Cl.
CPC ........... *A61M 11/00* (2013.01); *A61M 11/005* (2013.01); *A61M 15/0021* (2014.02);
(Continued)

(58) Field of Classification Search
CPC .... A61M 11/00; A61M 11/005; A61M 15/00; A61M 15/0001; A61M 15/001;
(Continued)

(56) References Cited

U.S. PATENT DOCUMENTS 4,300,546 A 11/1981 Kruber
4,674,491 A 6/1987 Brugger et al.
(Continued)

FOREIGN PATENT DOCUMENTS

EP 0171726 A2 2/1986
EP 1852896 A1 11/2007
(Continued)

OTHER PUBLICATIONS

English translation of Chinese Office Action dated Aug. 8, 2019 in connection with Chinese Application No. 201580010377.8.

*Primary Examiner* — Joseph D. Boecker
(74) *Attorney, Agent, or Firm* — Wolf, Greenfield & Sacks, P.C.

(57) ABSTRACT

Inhalator (50) comprising an aerosol generator (64) configured to generate an aerosol by nebulizing a fluid and a controller (24) configured to control operation of the aerosol generator and a housing (11, 51) accommodating at least the aerosol generator and the controller, the housing having a base (12) for supporting the housing on a horizontal surface, wherein a portion (35) of the housing accommodating at least a portion of the controller is arranged further away from the base than the aerosol generator as seen in a vertical direction, when the base is supported on the horizontal surface.

21 Claims, 4 Drawing Sheets

(51) Int. Cl.
  *A61M 16/04*  (2006.01)
  *A61M 16/06*  (2006.01)
  *A61M 16/00*  (2006.01)

(52) U.S. Cl.
  CPC ........ *A61M 15/0085* (2013.01); *A61M 16/04* (2013.01); *A61M 16/06* (2013.01); *A61M 15/0015* (2014.02); *A61M 2016/0015* (2013.01); *A61M 2205/35* (2013.01); *A61M 2205/50* (2013.01); *A61M 2205/581* (2013.01); *A61M 2205/586* (2013.01); *A61M 2205/8206* (2013.01); *A61M 2209/06* (2013.01); *A61M 2209/10* (2013.01)

(58) Field of Classification Search
  CPC .......... A61M 15/0013; A61M 15/0015; A61M 15/0021; A61M 15/0085; A61M 2205/50; A61M 2205/586; A61M 2205/8206; A61M 2209/10
  See application file for complete search history.

(56) References Cited

U.S. PATENT DOCUMENTS

| | | | |
|---|---|---|---|
| 4,922,901 A * | 5/1990 | Brooks | A24F 47/006 128/202.27 |
| 5,452,711 A * | 9/1995 | Gault | A61M 15/0085 15/85 |
| 7,891,352 B2 | 2/2011 | Gallem et al. | |
| 8,333,187 B2 | 12/2012 | Gallem et al. | |
| 2002/0020408 A1 | 2/2002 | Knauer | |
| 2003/0000520 A1 | 1/2003 | Ivri et al. | |
| 2005/0252508 A1 | 11/2005 | Koerner et al. | |
| 2006/0243274 A1 | 11/2006 | Lieberman et al. | |
| 2007/0062520 A1 | 3/2007 | Nobutani | |
| 2007/0289590 A1 | 12/2007 | Kreutzmann et al. | |
| 2008/0006264 A1 | 1/2008 | Gallem et al. | |
| 2010/0024814 A1 * | 2/2010 | Sugita | A61M 15/0021 128/203.14 |
| 2011/0108025 A1 | 5/2011 | Fink et al. | |
| 2011/0226236 A1 * | 9/2011 | Buchberger | A61M 11/041 128/200.23 |
| 2011/0290241 A1 | 12/2011 | Maeda et al. | |
| 2014/0116426 A1 * | 5/2014 | Mullinger | A61M 11/005 128/200.14 |
| 2014/0286630 A1 * | 9/2014 | Buchberger | A61M 11/041 392/395 |

FOREIGN PATENT DOCUMENTS

| | | |
|---|---|---|
| EP | 1875936 A1 | 1/2008 |
| EP | 2679265 A1 | 1/2014 |
| JP | 2005 278742 A | 10/2005 |
| WO | WO 2003/063937 A1 | 8/2003 |
| WO | WO 2004/041335 A1 | 5/2004 |
| WO | WO 2005/032630 A1 | 4/2005 |
| WO | WO 2011/088070 A1 | 7/2011 |
| WO | WO 2011/089485 A1 | 7/2011 |

* cited by examiner

INHALATOR AND INHALATOR SET

CROSS REFERENCE TO RELATED APPLICATIONS

This application is a national stage of PCT/EP2015/053930, filed Feb. 25, 2015, which claims priority to EP 14156519.2, filed Feb. 25, 2014, which are hereby incorporated by reference in their entirety.

TECHNICAL FIELD

The present invention relates to an inhalator and an inhalator set. In particular, the present invention relates to inhalators that are configured to nebulize a fluid for producing an aerosol to be inhaled by an individual. In general, the aerosol will contain an active ingredient, particularly a pharmaceutical ingredient for therapeutic purposes. However, also non-pharmaceutical solutions such as saline solutions may be used.

BACKGROUND

Such inhalators are generally configured of an aerosol generator unit and a controller unit containing the controller for controlling operation of the aerosol generator as part of the aerosol generator unit. In principle, there are two concepts for connecting the controller unit and the aerosol generator unit known in the art. One concept suggests to accommodate each unit in separate housings and electrically connect the controller and the aerosol generator by use of a relatively long (e.g. 1 m) cable. Such inhalators are for example distributed by Pari® as Eflow® Rapid or distributed by Aerogen® as Aeroneb® Go. Another disclosure in this regard may be found in US 2011/0108025 A1. Even though this kind of connection has proven beneficial in many regards, the use of a cable is under certain circumstances considered inconvenient for the user.

Other devices known in the art directly connect the aerosol generator unit and the controller unit in that both are located in a common separable housing. In those devices, the controller section is situated below the aerosol generator unit during use and when supported on a horizontal surface during non-use. Because of this configuration, the entire inhalator has a relatively large height and the center of gravity relative to a support surface is comparably high. Thus, if the inhalator is supported on the horizontal surface during non-use, the inhalator tends to tilt with the risk of dropping and damaging the inhalator. Such inhalators are for example distributed by Omron® as U22® or distributed by Health and Life as HL100.

Furthermore, either one of the above configurations have proven not very ergonomic during inhalation. The one was restricted in its use by the cable and the other was difficult to grip and perceived inconvenient due to an uncomfortable posture during inhalation.

In addition, it has been proven necessary in many regards and in order to lengthen the lifetime of the aerosol generator to provide some kind of cleaning unit. Such cleaning unit enables back flushing of the aerosol generator. Such a cleaning unit is described in more detail in EP 1 875 936 B1. Inserting the aerosol generator into the cleaning unit requires rotating the aerosol generator by 180° which poses no problem when using a cable for connection of the aerosol generator to the controller because the cable may be twisted. However, when using a configuration, in which the aerosol generator unit and the controller unit are integrated in one housing, those cleaning units may no longer be used.

When considering inhalators, in which the housing may be opened to e.g. remove the aerosol generator, the parts of the housing have to be locked when closed. For this purpose, a latch has been used comprising a lug having an opening at one end and integrally formed with one of the housing parts, and a protrusion at the other of the housing parts. The opening of the lug receives the protrusion for locking the parts together. The lug was in general integrally formed with the housing part using an integral hinge. Those integral hinges, however, had the drawback, that a "predetermined breaking line" was created at the hinge risking separation of the lug from the housing part after repeated use.

SUMMARY OF THE INVENTION

In view of the aforesaid, it is one object of the present invention to provide an inhalator that is more stable when supported on a horizontal surface preventing potential damaging of the inhalator by tilting and at the same time being more ergonomic.

Another object of the present invention is the provision of an inhalator for direct connection to an aerosol generator unit without the use of a cable and preferably still enabling back-flushing of the aerosol generator by means of a cleaning unit, and of a corresponding inhalator set.

An even further object of the present invention is the provision of an inhalator in which two housing parts of the inhalator may be securely connected and locked by means of a latch with an increased lifetime of the latch.

At least one of the above objects is solved by the subject matter of the independent claim 1, 16, 23 or 24. Embodiments of the present invention are derivable from the following description, the drawings as well as the dependent claims. In this context, it is self-evident that the aspect defined in one independent claim may also be combined with an aspect defined in other independent claim and the dependent claims depending on one of the independent claims may also depend on other independent claims. Thus, any combinations of features named in the claims and description are conceivable unless those combinations contradict each other. According to one aspect, an inhalator is suggested in which the housing containing the controller and particularly a portion of the housing actually containing a portion of the controller extends above and beyond the housing containing the aerosol generator and preferably the aerosol generator itself and even more preferred a fluid container for containing a fluid to be nebulized. Hence, the inhalator basically assumes a shape similar to the letter "L" with the vertical leg formed by the housing or part of the housing accommodating the controller and the horizontal leg formed by the housing or part of the housing containing the aerosol generator. By means of this configuration, one surprisingly obtains an ergonomic configuration that may be easily gripped and is perceived comfortable during inhalation. At the same time, this configuration enables lowering of the center of gravity thereby providing a more stable inhalator when supported on a horizontal surface reducing the risk of damaging the inhalator.

Hence, according to an aspect, an inhalator is suggested which comprises an aerosol generator. The aerosol generator is a device that enables the production of an aerosol from a fluid, particularly a liquid. This may preferably be achieved by using a vibratable membrane having a plurality of apertures through which the fluid is passed for nebulization. Such vibratable membranes are generally connected to a piezoelectric actuator for active vibration of the membrane (see e.g. EP 1 852 896 A1 incorporated in its entirety by reference). The vibration causes the fluid to pass through the apertures being nebulized on an opposite side of the membrane as compared to that side at which the fluid is applied.

The fluid may be applied via a fluid container configured to contain the fluid to be nebulized. The fluid container may be a space defined in a housing of the inhalator and being a non-separable part of the housing. Yet, the fluid container may also be formed by an insertable and replaceable ampoule or other container that may be coupled or uncoupled from the housing of the inhalator. The fluid container serves for supplying a fluid to be nebulized to the aerosol generator and, hence, the fluid container may be limited at one side by the aerosol generator, particularly the membrane thereof.

In order to operate the aerosol generator, that is in the example the piezoelectric actuator for vibrating the membrane, the inhalator comprises a controller. This controller is configured to control operation of the aerosol generator including starting and stopping of the aerosol production. The control may as well involve further functions such as detecting and processing of parameters, e.g. inhalation by a patient, amount of fluid available, etc. which may be used for monitoring and/or triggering the operation of the aerosol generator.

Moreover, the inhalator comprises a housing accommodating at least the aerosol generator and the controller. The housing has a base for supporting the housing on a horizontal surface, particularly in case the inhalator is not in use. Preferably, the inhalator is to be placed on the horizontal surface in the same orientation as during inhalation. Easy attachment of the fluid container, if configured replaceable, or easy filling of the fluid container, if integrally formed with the housing, should be enabled in this orientation. In the latter case, it is likely that a lid is attached to the fluid container which is to be removed for filling the fluid container. The lid should be easily accessible for removal and the opening of the fluid container should be directed vertically upward to enable easy filling when the inhalator is supported by its base on the horizontal surface.

For stable support of the inhalator on the horizontal surface, a portion of the housing accommodating at least a portion of the controller is arranged further away from the base than the aerosol generator as seen in a vertical direction, when the base is supported on the horizontal surface. "A portion of the housing accommodating at least a portion of the controller" also includes another portion of the housing which extends from that portion and does not accommodate the controller or a portion thereof which is arranged even further away from the base than said portion. That is, said portion does not necessarily form the top of the inhalator, even though this is preferred. As a result, the center of gravity is lowered and a more stable support of the inhalator on a horizontal surface may be achieved. In addition, this configuration provides for an ergonomic inhalator that may be easily gripped and held during inhalation by an individual or patient so that the inhalator is perceived comfortable and convenient to use.

As previously indicated, it is preferred that the inhalator is a so-called membrane inhalator, wherein the aerosol generator has a vibratable membrane with a plurality of apertures through which the fluid is passed for nebulization. It is even more preferred that said portion of the housing which accommodates the portion of the controller is arranged further away from the base than the membrane as seen in the vertical direction, when the base is supported on the horizontal surface. This enables an inhalator with a relatively low total height as compared to the prior art even though the controller and the aerosol generator are accommodated in a common housing and not connected via a cable.

Further, to improve the ability to fill or replace the fluid container and/or ease of direct connection (without a cable) of the aerosol generator to the controller, it is preferred that the membrane is oriented substantially parallel to the base of the housing. That is, during use or when the inhalator is supported, the membrane is oriented substantially horizontal. The term "substantially" in this regard indicates that the orientation does not need to be exactly parallel or horizontal. Rather, a variation in the range of ±30°, preferably ±15° would still be considered within the scope of this term.

The controller may comprise a circuit board and at least a portion of the circuit board is accommodated in said portion of the housing. As a consequence, at least a portion of the circuit board, namely that portion which is accommodated in said portion of the housing which is arranged further away from the base and preferably the aerosol generator, is also arranged further away from the base and preferably the aerosol generator as seen in the vertical direction, when the base is supported on the horizontal surface.

The prior art reveals several possibilities to apply the liquid to the aerosol generator, such as by capillary forces, wicks or pumps, which actively convey the fluid to the aerosol generator. However, the present inhalator is particularly designed for an aerosol generator that is gravity fed. "Gravity fed" defines that the fluid is flown to the aerosol generator, i.e. applied to the aerosol generator (its membrane, if present), primarily by gravitational force. This very much simplifies the construction of the inhalator as no additional elements such as pumps or wicks are required.

As previously indicated, a fluid container containing the fluid to be nebulized may be arranged on an opposite side of the aerosol generator (its membrane, if present) relative to the base, that is above the aerosol generator. It is preferred that said portion of the housing is even arranged further away from the base than the fluid container as seen in the vertical direction, when the base is supported on the horizontal surface.

The inhalator is preferably configured so as to lower the center of gravity. For this purpose, it may be beneficial to place elements having a larger weight than others closer to the base. For example, a battery compartment to supply power to the controller has contacts to receive and electrically contact one or more batteries. The contacts are configured so that the battery/-ies are located closer to the base than to a top of the inhalator at an opposite side of the base and furthest away from the base. Hence, an inhalator in which the center of gravity of the inhalator is closer to the base than to the top is preferred. That is, in a side view drawing a horizontal line and contacting the lowest point of the housing of the inhalator at the base and another horizontal line contacting the highest point of the housing of the inhalator at the top defines the height and the center of gravity is located closer to the lower line than to the upper line. In an even more preferred embodiment, the center of gravity is located in the lower third of the height, preferably in the lower quarter of the height.

In order to enable gripping and holding of the inhalator during inhalation, it is preferred that the portion of the housing accommodating at least a portion of the controller forms a handle so that the inhalator may be held during inhalation with the base facing downward. The grip may be exclusively formed by said portion, but it is preferred that said portion is only a part of the grip.

Moreover, the inhalator may comprise an outlet for delivery of the nebulized fluid to a patient. The outlet is preferably located closer to the base than the aerosol generator and said portion of the housing as well as the fluid container. Preferably, the outlet has a center axis which is substantially parallel to the orientation of a membrane of the aerosol generator. That is, the center axis of the outlet and a center axis of the membrane are angled relative to each other. This in addition to the orientation of the membrane parallel to the base enables the configuration of an inhalator with a low height, which is also advantageous regarding stability of the inhalator when placed on a horizontal surface.

According to an aspect of the invention, the housing of the inhalator is separated into a first housing accommodating the controller and a second housing accommodating the aerosol generator, wherein the first and second housing being detachably connected.

As previously indicated, it is preferred to avoid a cable for connecting the aerosol generator and the controller. Accordingly, it is preferred that the first and second housing are directly connected to each other. This may be achieved in that one of the first and second housings comprises a socket and the other of the first and second housings comprises a plug detachable from and electrically connected (connectable) to the socket. Thereby, it is easily possible to directly connect the two housings and, hence, the controller and the aerosol generator. The terms "plug" and "socket" in the present invention apply to all kind of electrical connectors that may establish electrical contact by plugging that is mating two parts. Plug and socket connectors are usually made up of a male plug (typically pin contacts) and a female receptacle (typically socket contacts). However, in the present application the term is not limited to this understanding. Rather, the socket is considered as the "non-movable part" of the connector into which the plug, as the "movable part" of the connector is introduced no matter whether the socket is female or male and the plug is male or female. Further, also hermaphroditic do also fall within this scope.

The direct connection of the two housings poses the problem that conventional cleaning devices may no longer be used as those require flipping of the aerosol generator by 180°. The connection of the aerosol generator and the controller was achieved in the prior art by a cable and the cable was twisted to absorb the 180° rotation. When directly connecting the first and second housings, however, a new solution is required. Accordingly, it is suggested in one embodiment that the socket or the plug is configured to receive the plug or the socket at least in two different orientations. The two different orientations are preferably rotated by 180° relative to a center axis (preferably a symmetry axis) of the socket.

In addition, it may be required to lock the first and second housings to each other. This may be achieved by a latch. In the prior art, such latch was configured by a lug integral with and extending from one of the first and second housings and having a hole engaged with a protrusion integral with the other of the first and second housings. In order to engage and disengage the lug with the protrusion, an integral hinge was provided. This is of course also conceivable with respect to the present invention. Yet, an integral hinge being exposed to repeated bending-stress bears the risk that after a certain lifetime, the lug breaks and separates from the housing at the integral hinge forming a "predetermined break line". To solve this problem, a lug is suggested having a flexible area which extends a certain distance in a direction away from the connection to one of the first and second housings towards the hole. Thereby, the lug may not be rotated about a strict axis or hinge, but may be flexed in the flexible area. This flexure of the lug relative to the one of the first and second housings enables disengagement from and engagement with the protrusion. In addition, the "predetermined break line" which was disadvantageous in prior art systems is avoided and separation of the lug can be securely prevented.

According to an embodiment, the lug remains flexed after the disengagement from the protrusion, meaning that it does not spring back into the engagement position. For engagement, it is again necessary to actively bend the lug in the flexible area to engage it with the protrusion by flexure. This is advantageous from the perspective, that a user perceives an optical and preferably also an audible feedback that the two housings are securely connected and locked.

According to another aspect and to solve also at least one of the afore-mentioned objects, an inhalator comprising a controller unit and an aerosol generator unit is suggested. The controller unit comprises a first housing, a controller accommodated in the first housing and a socket electrically connected to the controller. The socket may be accessible via an opening in the first housing or protrude from the first housing. The controller unit may of course comprise additional elements such as another socket for connection to a personal computer or to a power source by means of e.g. a USB cable. In addition, a battery compartment may be contained in the controller housing as mentioned above. Furthermore, the controller housing may comprise an ON/OFF button to start and stop inhalation and cooperating with a switch of the controller. The aerosol generator unit comprises a second housing and an aerosol generator accommodated in the second housing. Further, a plug is provided which is configured to detachably connect with the socket of the controller unit. The plug is electrically connected to the aerosol generator and may be accessible via an opening in the second housing or protrude from the second housing. Thus, the controller unit and the aerosol generator unit are directly connectable without the need of a cable but by directly mating the plug and the socket. To avoid repetition, the controller unit and the aerosol generator unit may be configured as described above.

In order that the inhalator may also be used with a cleaning unit for cleaning the aerosol generator, it is preferred that the socket or the plug is configured to receive the plug or the socket in at least two different orientations, preferably orientations that are offset by 180° for establishing an electrical connection between the plug and the socket.

To achieve such a configuration, the socket may comprise a circuit board having two opposite sides and each side comprises a conductive path for electrical connection to electrical contacts of the plug. In one orientation, the one conductive path on one side of the circuit board and another conductive path on the opposite side connect to a respective contact of the plug. These contacts preferably are formed by elastic contact tongues being urged towards the respective side of the circuit board. In the other orientation, rotated by 180° for example, two other elastic contact tongues are urged towards the respective side of the circuit board and contact the same respective conductive path of the circuit board (also described later).

In order to enable the inhalator being stably supported on a horizontal surface, particularly when connected to the aerosol generator, it is preferred that the first housing has a base for supporting the housing on the horizontal surface, wherein the socket is located closer to the base of the first housing than to a top of the first housing as seen in a vertical direction, when the base is supported on a horizontal surface.

According to one embodiment and for ease of assembly, the controller comprises a circuit board and the socket is electrically connected to one side of the circuit board by means of an elastic contact (Combination of elastic contact and contact area) or a plug/socket connection, and a power supply, such as the contacts of a battery compartment for connecting to a battery/-ies for power supply to use the inhalator as stand-alone unit, is electrically connected to the opposite side of the circuit board by means of an elastic contact (Combination of elastic contact and contact area) or a plug/socket combination.

Further, the elastic contact/contact area connection or plug/socket connection enables that the circuit board is connected to the power supply and the socket by assembly of these elements without the need of a contacting step such as welding, soldering, etc.

Moreover, an inhalator set is suggested comprising a controller unit as described above and an aerosol generator unit as described above. The plug of the aerosol generator contained in the aerosol generator unit is electrically connectable to the socket in a first orientation. Further, the inhalator set comprises a cleaning unit configured to clean the aerosol generator, particularly by reflushing as described in EP 1 875 936 B1 (incorporated in its entirety herein by reference). For this purpose, the cleaning unit may have a cleaning solution compartment for receiving a cleaning solution. The cleaning solution compartment is preferably at a lower end closed by the aerosol generator, particularly its membrane, when the aerosol generator is inserted into the cleaning unit. For this purpose, the cleaning unit has a third housing with a receiving section for receiving the aerosol generator. The third housing has an opening for giving access to the plug of the received aerosol generator or the plug protrudes from the third housing so that the plug is electrically connectable to the socket in a second orientation different from the first orientation. By means of this set, it is possible to remove the aerosol generator from the aerosol generator unit. This may be achieved by opening the second housing removing the aerosol generator completely. Alternatively, the second housing is separated into two parts one containing the aerosol generator and the other containing a nebulization chamber into which the fluid to be nebulized is introduced. Subsequently, the aerosol generator as such or together with the part of the second housing is inserted into the receiving section of the cleaning unit turned by 180°. Thereby, also the plug of the aerosol generator is turned by 180°. Because of the configuration of the socket and the plug, however, the plug and the socket can mate in both orientations.

To achieve such a configuration, the socket may comprise a circuit board having two opposite sides and each side comprises a conductive path for electrical connection to electrical contacts of the plug. In one orientation, the one conductive path on one side of the circuit board and another conductive path on the opposite side connect to a respective contact of the plug. These contacts preferably are formed by elastic contact tongues being urged towards the respective side of the circuit board. In the other orientation, rotated by 180° for example, two other elastic contact tongues being urged towards the respective side of the circuit board contact the respective conductive path of the circuit board.

In order to enable the inhalator being stably supported on a horizontal surface, particularly when connected to the aerosol generator, it is preferred that the first housing has a base for supporting the housing on the horizontal surface, wherein the socket is located closer to the base of the first housing than to a top of the first housing as seen in a vertical direction, when the base is supported on a horizontal surface.

Further, it is preferred that the second and/or third housing have a bottom and a top, wherein the plug of the aerosol generator is located closer to the top than to the bottom, when the inhalator is in use. This again enables a relatively low height inhalator which may be stably supported on a horizontal surface. This further enables that the center of gravity be lowered.

According to an even further aspect of the invention, an inhalator is suggested to solve at least one of the above objects. The inhalator comprises a housing with a first housing and a second housing. The first housing and the second housing may be a first housing containing a controller and a second housing containing an aerosol generator. However, the first housing and the second housing may as well be two parts of the (second) housing accommodating the aerosol generator. As a result, removal of the aerosol generator from the housing as such or together with a part of the housing that accommodates the aerosol generator is possible. First and second housings are detachably connected by a latch. The latch mechanism comprises a lug having a flexible area which extends a certain distance in a direction away from the connection to one of the first and second housings towards the hole. Thereby, the lug may not be rotated about a strict axis or hinge, but may be flexed in the flexible area. This flexure of the lug relative to the one of the first and second housings enables disengagement from and engagement with the protrusion. In addition, the "predetermined break line" which was disadvantageous in prior art systems (see above) is avoided and separation of the lug can be securely prevented.

According to an embodiment, the lug remains flexed after the disengagement from the protrusion, meaning that it does not spring back into the engagement position. For engagement, it is necessary to actively bend the lug in the flexible area to engage it with the protrusion by flexure. This is advantageous from the perspective, that a user perceives an optical and preferably also an audible feedback that the two housings are securely connected and locked.

Further features and embodiments of the present invention are also disclosed in the following description of a preferred embodiment. The features may certainly be combined with any of the aforesaid features in an arbitrary manner unless the features contradict each other.

BRIEF DESCRIPTION OF THE DRAWINGS

The description of the preferred embodiment makes reference to the accompanying drawings, in which:

FIG. 9a shows the process of connecting the aerosol generator unit and the controller unit and 9b in the connected state in a perspective view from the bottom;

DESCRIPTION OF AN EMBODIMENT OF THE INVENTION

In the drawings, the same elements have been designated by the same reference numerals.

Figure 1:
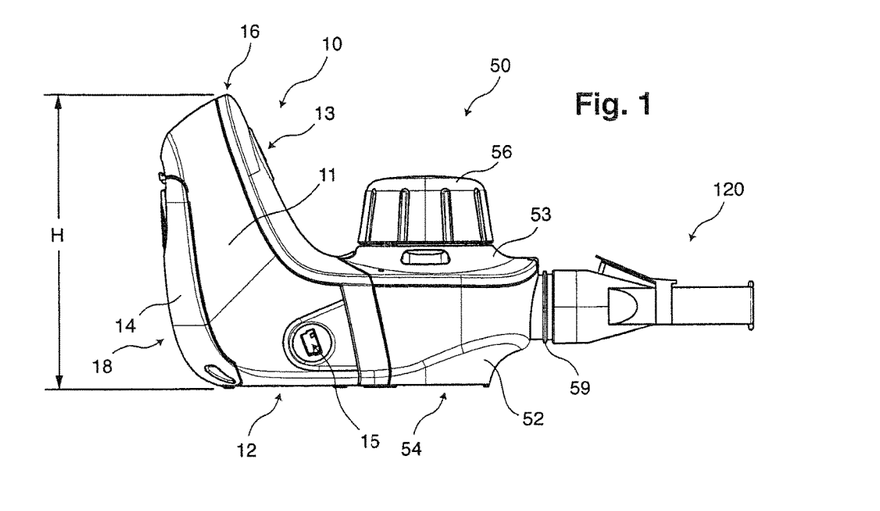
FIG. 1 shows an inhalator according to the present invention in a side view.

The inhalator as shown in FIG. 1 comprises a controller unit 10 and an aerosol generator unit 50 which are connected to each other. Further, a mouthpiece 120 is provided.

The controller unit 10 has a housing (the first housing) 11. The housing has at its lower end a base 12 for supporting the inhalator on a horizontal surface such as a desk. Integrated into the housing 11 is an ON/OFF button 13 and a battery compartment lid 14 that is removable from the housing 11 for exchanging batteries. A USB socket 15 is provided at one side of the housing 11, which may be used for connection to a power supply and/or charging the batteries in the battery compartment and/or for connection of the inhalator to a personal computer.

A top 16 is defined opposite to the base 12, wherein the total height H of the inhalator is defined between the base 12 and the top 16. The height H of the inhalator preferably resides between 20 and 120 mm, preferably between 40 and 100 mm. Hence, the inhalator is preferably not higher than 150 mm, more preferably not higher than 120 mm, and most preferably not higher than 100 mm.

Figure 11:
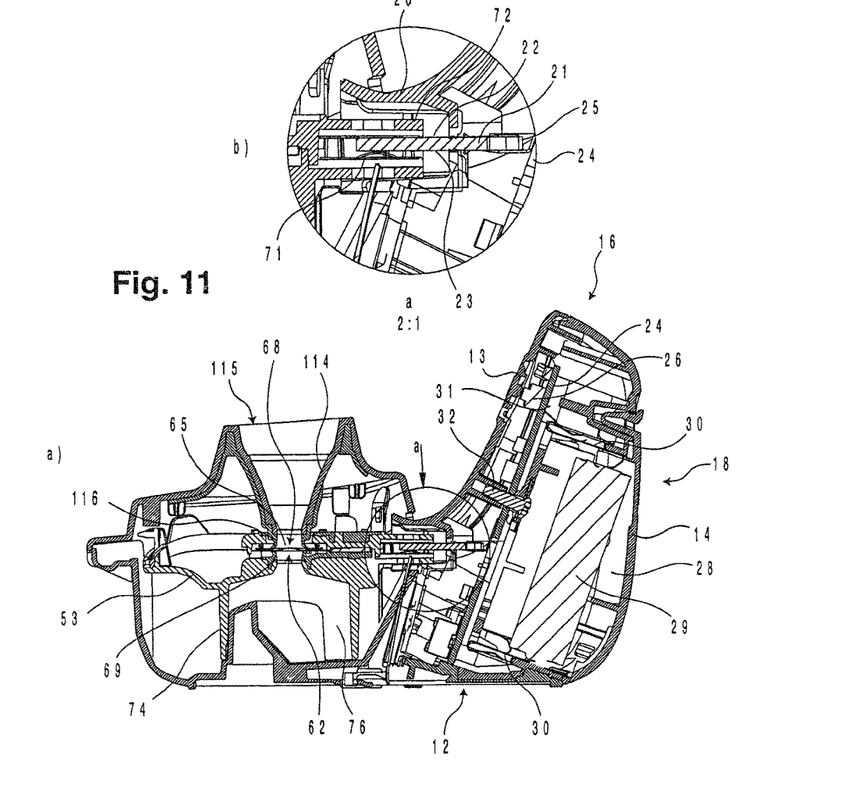
FIG. 11 shows a) a longitudinal section through the inhalator connected to the cleaning unit as shown in FIG. 8 and b) the portion of the plug and socket in enlarged scale.

The controller unit 10 further has a front 17 (see FIG. 7) and a back 18. The battery compartment lid 14 is located at the back 18. A socket 19 is provided at the front 17 of the controller unit 10 as best visible from FIG. 7. The socket comprises a circumferential wall 20 which in the present embodiment forms a rectangular space. However, other cross-sectional shapes are conceivable such as circular, oval, etc. A circuit board 21 extends from the controller housing 11 into the rectangular space (see FIG. 11b). The circuit board 21 has opposite sides 22 and 23 on each of which there are provided conductive paths (not visible in the drawings). The circuit board 21 is connected to a controller circuit board (controller) 24, preferably also by means of a plug and socket connection 25.

The circuit board 24 within the controller housing 11 is oriented vertically, that means that it extends from the base 12 to the top 16 and it is rather directed to a vertical line than to a horizontal line meaning that it is angled within a range of 45° and 90° to a horizontal axis. The controller housing 11 has a portion 35 containing a portion of the controller circuit board 24 that resides above the aerosol generator as described later.

A switch 26 is located on the circuit board below the bottom 15. Batteries 29 in the battery compartment 28 are connected to battery contacts 30 which again are contacted to the controller circuit board 24 by mere contact of elastic contacts at the position 31.

The controller circuit board 24 is only secured to the controller housing 11 by one screw 32 wherein a conductive path of the controller circuit board 24 is electrical contact with the battery contact 30 at the position 31 so that no complicated assembly is required. In addition, the circuit board 21 is connected to the socket circuit board 24 by plug socket connection 25, the socket circuit board being fixed in the controller housing 11. Also in this case, no complicated assembly is required.

The batteries 29, disposed in the battery compartment 28, are located closer to the base 12 than to the top 16, that is the contacts 30 contacting the batteries 29 are located so that the batteries 29 are located closer to the base 12 than to the top 16 if inserted into the battery compartment 28.

Figure 9:
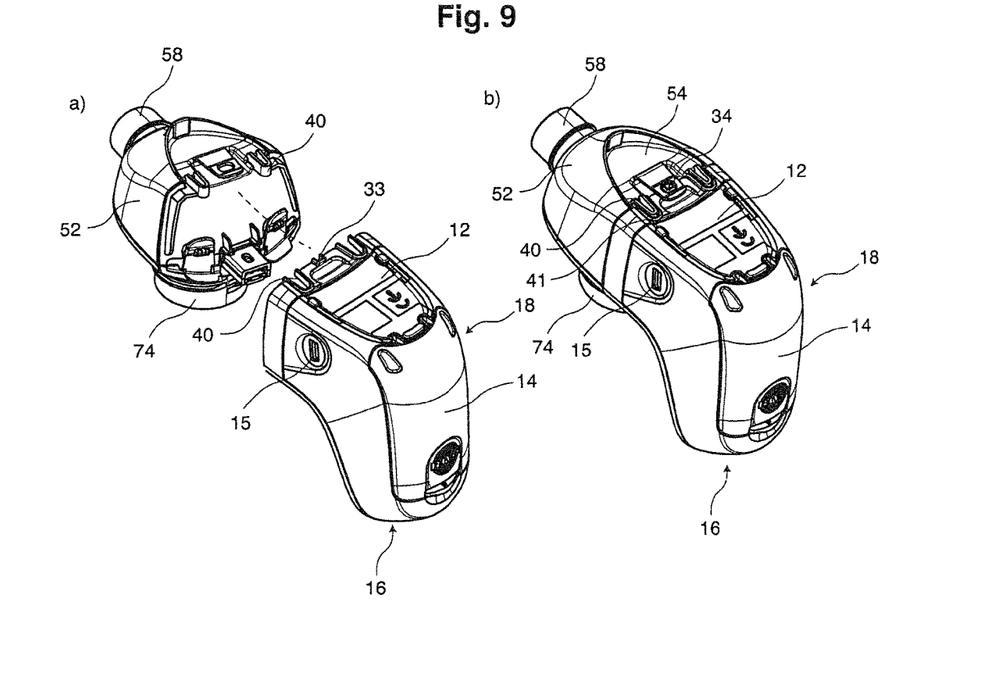

As is best visible from FIG. 9, a protrusion 33 of a latch 34 is integrally formed with the controller housing 11. This latch 34 is described in more detail below and is for connection of the controller unit 10 to the aerosol generator unit 50 or the cleaning unit 100.

Next, the aerosol generator unit 50 is explained with respect to FIGS. 2 to 4 and FIG. 10. The aerosol generator unit 50 has an aerosol generator housing (second housing) 51 which is separated into a first housing part 52 and a second housing part 53. The aerosol generator housing 51 comprises a bottom 54. A top 55 of the aerosol generator unit 50 opposite to the bottom 54 is formed by the lid 56.

Figure 2:
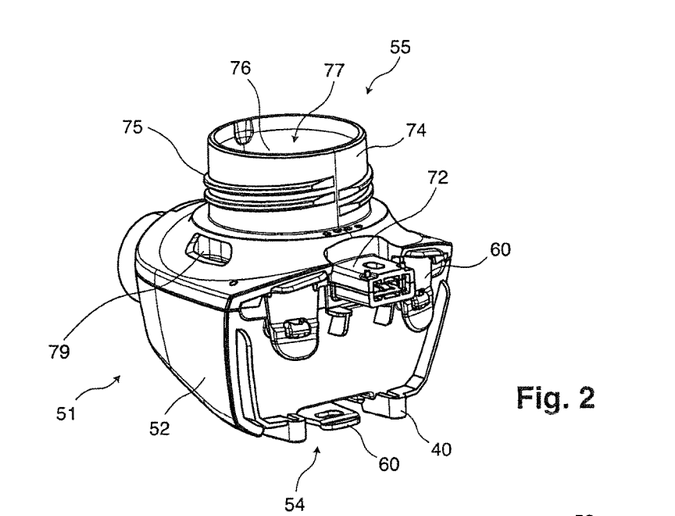
FIG. 2 shows a perspective of a second housing accommodating the aerosol generator with a lid closing a fluid container being removed.
Figure 3:
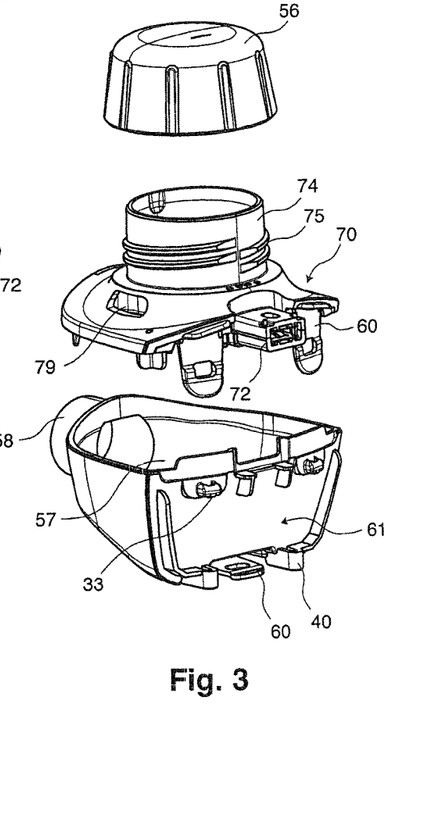
FIG. 3 shows an exploded perspective view of the second housing in FIG. 2 including the lid.
Figure 4:
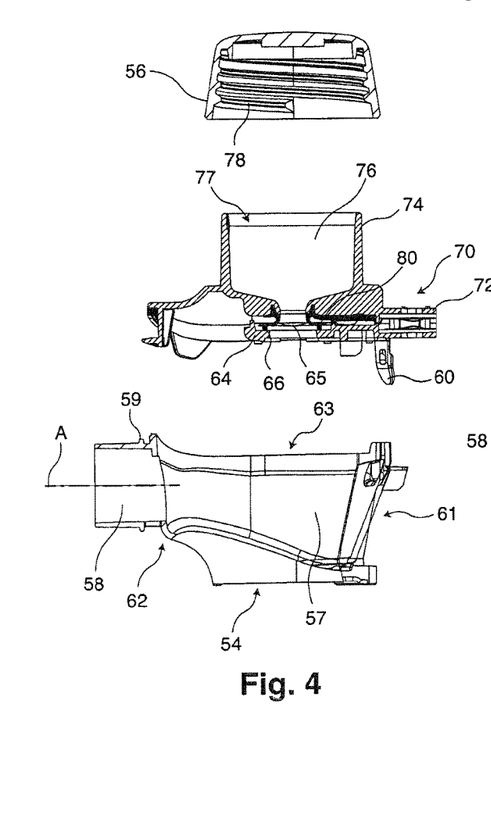
FIG. 4 shows an exploded view of FIG. 3 in cross-section.

The first housing part 52 forms a nebulization chamber 57 into which the aerosol is introduced during operation of the aerosol generator. An outlet 58 having a center axis A is connected to the nebulization chamber 57. The outlet 58 is configured so that a mouthpiece 120, or a mask, or face mask, nasal prongs, or ventilator tube or endotracheal tube, or other equipment may be attached. This purpose, the outlet 58 can be configured as a Luer connection. In addition, at least one rib 59 may be provided so that a tube may as well be connected.

In addition, the first housing part has at the bottom 54 a lug 60 of the latch 34 explained in more detail later. In addition, two protrusions 33 of a latch mechanism 34 are provided integrally with the first housing part 52 at a back 61 facing the front 17 of the controller unit 10. The outlet 58 is disposed at the front 62 opposite to the back 61. The housing 52 has an opening 63 at its top which is to be closed by the second housing part 53.

The second housing part 53 comprises the aerosol generator 64 which is fixed in the second housing part 53 so as to be non-separable. The aerosol generator 64 comprises a membrane 65 which is vibratable by means of a piezoelectric actuator 80. The membrane 65 has a plurality of minute apertures (not visible in the drawings) and has a first side 67 and an opposite side 68.

The membrane 65 is vibratable held between a lip seal 69 on the first side 67 and another O-ring 66 at the opposite side 68 as described in DE 102005006375 (U.S. Pat. Nos. 7,891,352, or 8,333,187) incorporated in its entirety by reference.

Electrical contacts 71 are electrically connected to the piezoelectric actuator 80 and extend to the back 70 of the second housing part 53 at which electrical contacts are accessible. The elastic contacts 71 are formed facing each other with a space formed between them. The elastic electrical contacts 71 which are elastic in opposite directions extend into a space formed by a rectangular circumferential wall forming a plug 72. Particularly, two parallel and symmetrically arranged electrical elastic contacts 71 are located at on side of the space (circumferential wall) and another two parallel and symmetrically arranged electrical elastic contacts 71 are located at on opposite side of the space (circumferential wall). A first electrical contact 71 at a first side and a second electrical contact 71 at the opposite second side form a first pair to be contacted to conductive paths on respective sides 22 and 23 of the socket circuit board 21 in a first orientation. A third electrical contact 71 at the first side and a fourth electrical contact 71 at the second opposite side from a second pair to be contacted to the same conductive paths on respective sides 22 and 23 of the socket circuit board 21 in a second orientation rotated by 180°.

Further, the second housing part 53 has a boss 74 with an outer thread 75 forming the fluid container 76 which is closed at its lower end by the upper side 67 of the membrane 65. The boss has an opening 77 at its upper end into which a fluid to be nebulized may be filled. The opening 77 may be closed by means of the lid 56, which has an inner thread 78 to be screwed on the outer thread 75 of the boss 74.

Further, the second housing part 53 has at its back 70 two lugs 60 of latches 34 as described later in more detail.

Furthermore, two openings 79 are formed in the second housing part 53 which serve as vents during inhalation, wherein air is drawn in through the opening 79 into the mixing chamber (nebulization chamber) 57 on its way to the outlet 58. Preferably, one-way valves, preferably flap valves, are disposed in the opening 79 so as to allow a flow of air from the outside to the inside only.

Figure 10:
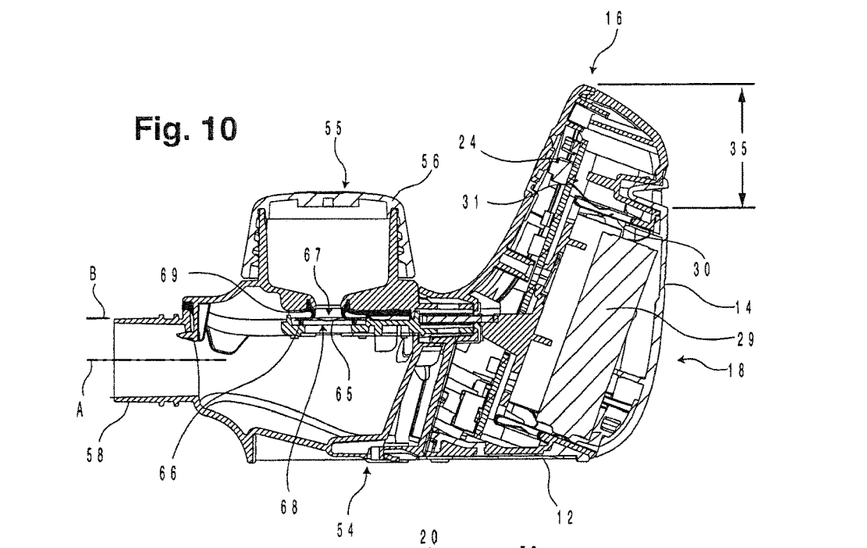
FIG. 10 shows a longitudinal section through an inhalator as shown in FIG. 1 with the mouthpiece being removed.

The outlet 58 has a center axis A parallel to the membrane 65 (parallel extension of the membrane has been visualized by the broken line B in FIG. 10) and is positioned closer to the bottom 54, and in a state connected to the controller unit 10, the base 12, than the membrane 65.

Figure 5:
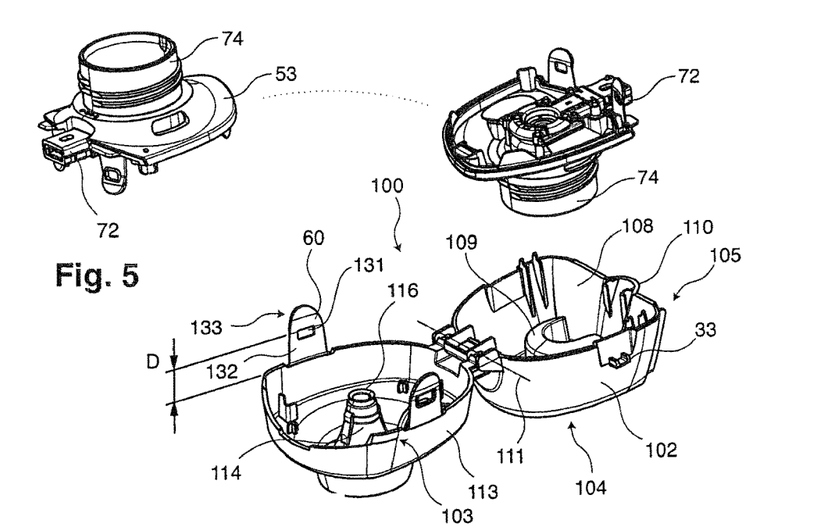
FIG. 5 shows an exploded perspective view of a cleaning unit during insertion of the aerosol generator including a part of the second housing as shown in FIGS. 2 to 4 in its receiving section.
Figures 6, 7, 8:
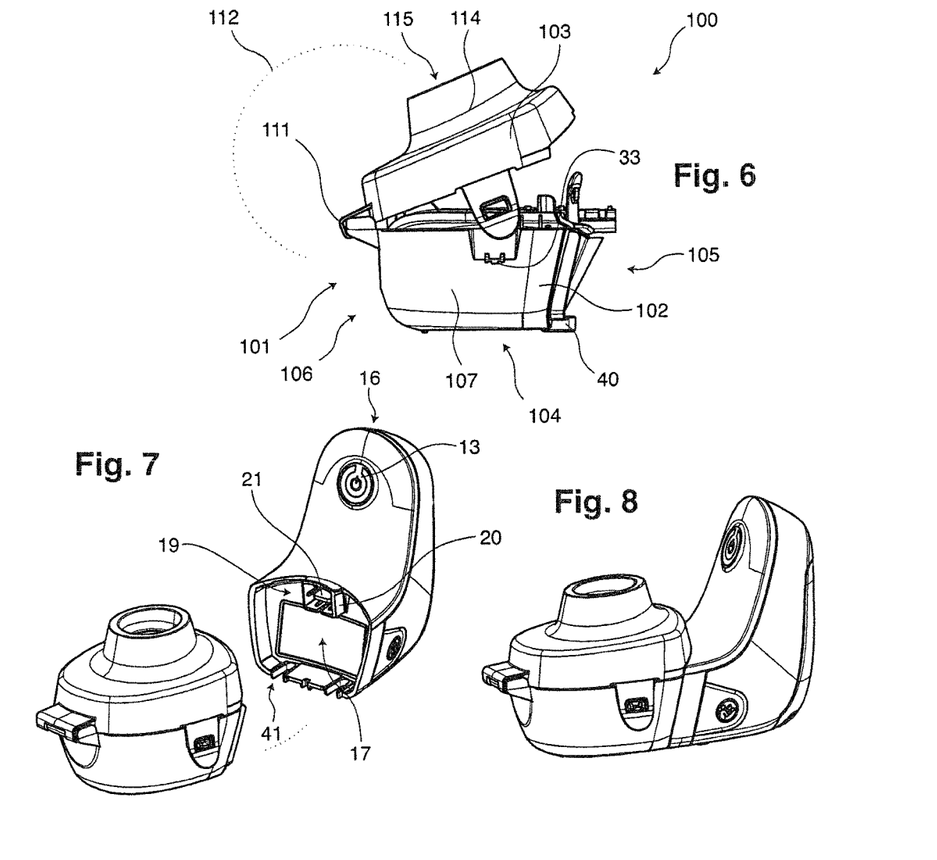
FIG. 6 shows a side view of the cleaning unit in the process of closing the third housing with the aerosol generator being received in the receiving section.
FIG. 7 shows a perspective view during the process of connecting the cleaning unit (third housing) and the controller unit (first housing)
FIG. 8 shows a perspective of the connected cleaning unit and controller unit in perspective.

Next, a cleaning unit 100 as shown in FIGS. 5 and 6 is described. The cleaning unit 100 has a cleaning unit housing (third housing) 101 comprising a first housing part 102 and a second housing part 103.

The first housing part 102 is considered as the lower housing part and has a bottom 104, a front 105 directed in the connection state toward the controller unit 10 and a back 106 at an opposite side. Protrusions 33 of a latch 34 are provided on opposite side walls 107 of the first housing part 102. The first housing part 102 defines a receiving section 108 which is configured to receive the second housing part 53 of the aerosol generator unit 50. A centering boss 109 is disposed at the bottom of the receiving section 108 for centering the fluid container 76 and particularly its boss 74 within the receiving section 106 (see FIG. 11a). A spout 110 is disposed at the front 105 of the first housing part 102. The second housing part 103 is hinged to the first housing part 102 at the back 106 so that the second housing part 103 may be rotated about an axis 111 as indicated by the dotted line 112 in FIG. 6 to provide access to the receiving section 108. Lugs 60 of a latch 34 are provided at side walls 113 of the second housing part 103.

In addition, the second housing part 103 comprises a funnel-shaped fluid reservoir 114 with an opening 115 at the top of the second housing part 103. The funnel-shaped fluid reservoir 114 has a lip seal 116 at its lower end for sealing against the membrane 65 of the aerosol generator unit 50.

Next, the latch 34 used at several locations is explained with reference to the latch 34 used for the cleaning unit 100 as shown in FIGS. 5 and 6. This explanation, however, also applies to the other latches 34 used at other positions.

Each latch 34 comprises a lug 60 which is integrally formed with the corresponding part, here the second housing part 103. The lug 60 extends away from the housing part 103. Further, the lug 60 has a cutout 131. An area at that side of the cutout 131 facing away from the connection to the second housing part 103 is bent away, that is towards the outside to form a gripping part 133. In addition, between the connection of the lug 60 to the second housing part 103 and a cutout 60 there is formed a flexible area 132 which extends a certain distance D from the connection of the lug 60 to the second housing part 103 towards the cutout 131. The lug 60 is flexible in this flexible area 32 and may be bent towards and away from the second housing part 103. This bending is partially plastic deformation so that the lug 60 to certain extent will remain in its bent position rather than springing back to its original position.

Moreover, the latch 34 comprises a protrusion 33 which is integrally formed with the first housing part 102, particularly at its side wall 107. In order to close the latch 34, one would tilt the first housing part 103 about the axis 111 closing the first and second housing part 102 and 103. Thereby, the lugs 60 at the sides override the protrusions 33. By actively flexing the lugs 60 towards the first housing part 102, the cutouts 131 engage with the protrusions 33 and the lug 60 remains in this position being bent towards the second housing part 102. Thereby, the user receives an audible signal such as click and also visibly recognizes a secure connection, because he has to actively move the lug 60 into engagement the protrusion 33 in contrast to conventional snap mechanisms in which the latches automatically snap into engagement.

Further, it may be beneficial to additionally provide guiding elements at each housing 11, 51 and 101 to assist the process of connecting the housings 11, 51 and 101. Such guiding elements may be formed as one example by a longitudinal protrusion 40 at one of the housings and a longitudinal recess 41 at the other of the housings. During the process of connecting the housings, the protrusion 40 engages with the recess 41 and translationally guides the housings until the housings are fully connected. Subsequently, the housings may be locked by means of the latch 34 as described earlier.

Preferably, two such protrusions 40/recesses 41 are provided in parallel to prevent tilting of one housing relative to the other housing during the connection process. Yet, other numbers and configurations of guiding elements are conceivable as well.

Next, the effect and function of the described embodiment is explained.

As will be best visible from FIG. 10, a portion of the housing 11 of the controller unit 10 that contains a portion of the controller, namely the controller circuit board 24 that is referenced to as the portion 35 extends beyond the aerosol generator, here the membrane 65. Thus, the portion 35 is located further away from the base 12 or the bottom 54 respectively than the aerosol generator, i.e. the membrane 65. In addition, at least a part of this portion extends beyond the top 55 of the aerosol generator unit 50 and particularly the lid 56.

Moreover, the battery compartment 28 comprising the batteries 29 is configured so that the batteries 29 are positioned closer to the base 12 than to the top 16.

Those measures have the effect that the entire height H as shown in FIG. 1 of the inhalator (controller unit 10 and aerosol generator unit 50 being connected) is relatively low. In addition, these measures serve to lower the center of gravity towards the base 12. Thereby, it is possible to provide an inhalator, which may stably be positioned on a support surface with its base 12 and the risk of the inhalator becoming damaged by tilting and dropping can be prevented.

At the same time, the controller housing 11 and particularly the portion 35 as part thereof form a grip for holding the inhalator during inhalation. Even though this configuration at first glance appears not very ergonomic, it has been proven very comfortable and convenient to use, particularly by one hand only.

The comfortable use is further enhanced in that the controller unit 10 and the aerosol generator unit 50 are connected without the use of a cable. In particular, considering the aerosol generator unit 50 shown in FIG. 2, one merely needs to connect the plug 72 to the socket 19. As best shown in FIG. 10, this is achieved in that the circuit board 21 with the not shown conductive paths on the opposite sides 22 and 23 is inserted into the aforesaid space between the elastic contacts 71 of the plug 70 of the aerosol generator. Thus, as shown in FIG. 9 by the dotted line, the aerosol generator unit 50 is merely translated towards the controller unit 10, whereby the plug 70 and the socket 19 mate, that engage and electrically connect.

To lock the two housings 11 and 51, one merely needs to flex the lug 60 at the bottom 54 of the aerosol generator housing 51 in its flexible area 132 towards the base 12 of the controller housing 11 until the cutout 130 engages with the protrusion 33 as shown in FIG. 9b.

Subsequently, the inhalator may be placed on a horizontal surface with its base 12 facing downward. By filling a fluid into the fluid container 76 through its opening 77 and closing the lid 56 by screwing, the inhalator is ready for use, wherein the liquid applies at the side 67 of the membrane 65.

In order to expand the lifetime of the aerosol generator, it is in many cases necessary and beneficial to use a cleaning unit 100. In the art, such as described in EP 1 875 936 B1, this has been achieved by inserting the aerosol generator into the cleaning unit and attaching the cable the aerosol generator. As the aerosol generator has to be tilted by 180° for enabling reflushing, the cable had been twisted by 180° as well. This, however, is not possible in a device as explained above which intends to omit any cable during inhalation. As such, the aerosol generator unit 10 is configured with a two-part housing having the first and second housing parts 52 and 53. These parts may be separated in that the lugs 60 shown in FIG. 2 are gripped at the gripping portion 133 and flexed in its flexible area 132 away from the back 61 of the first housing part 52. As a result, the cutouts 130 disengaged with the protrusions 33 and the second housing part 53 may be removed from the first housing part 52 as shown in FIG. 3. Additionally, the lid 56 is removed from the boss 74. The aerosol generator 64 including the membrane 65 is preferably fixed to the second housing part 53 and may not be removed from this part 53. Having removed the second housing part 53 and the lid 56 as shown in FIG. 5, the second housing part 53 is rotated by 180°. Subsequently, the second housing part 53 together with the aerosol generator 64, particularly the membrane 65 is inserted into the receiving section 108 of the cleaning unit 100, the centering boss 109 and the fluid container 76, particularly the boss 74 engage for centering the aerosol generator 64 and particularly the second housing part 53 within the receiving section. Thereby, also the plug 72 is rotated by 180°.

Subsequently, the cleaning unit may be closed by rotating the second housing part 103 relative to the first housing part 102 and engaging the lugs 60 and particularly their cutouts 130 with the protrusions 33 at the sides 107 of the first housing part 102. Thus, the cleaning unit is closed and may be connected to the controller unit. Particularly, the cleaning unit 100 is as well translated towards the controller unit 10, whereby the plug 70 and the socket 19 electrically insert into each other to obtain an electrical connection between the elastic contacts 71 and the circuit board 21. Thereby, the wall 73 inserts into the wall 20. Subsequently, the lug 60 of the cleaning unit 100 is engaged with the protrusion 33 of the controller unit as described with respect to the aerosol generator unit in FIG. 9. Thus, the cleaning unit 100 and the controller unit 11 are securely fixed to each other. Even though, the aerosol generator and, hence, the plug 70 have been rotated by 180° as shown in FIG. 5 and because of the configuration of the plug 70 and the socket 19 is still possible to mate the plug 70 and the socket 19 in the same manner, namely a translational movement. Thus, a cable can be omitted and operation of the inhalator be facilitated for a user.

To perform reflushing, a cleaning solution is introduced through the opening 115 into the funnel-shaped fluid reservoir 114 applying at the side 68 of the membrane 65. Subsequently, the aerosol generator is operated by pressing the button 15. The fluid to be nebulized as well as the cleaning solution is fed to the membrane 65 by gravitational force. The cleaning solution is collected as shown in FIG. 11 within the first housing part 102 and may after cleaning be poured out through the spout 110.

Finally, because of the latch 34 enabling all connections, separate housing parts may be easily connected and locked to each other which applies to the aerosol generator unit 50 as such, the cleaning unit 100 as such as well as the connection of the controller unit 10 with the aerosol generator unit 50 and the cleaning unit 100. This further facilitates the use of the set.

The invention claimed is:

1. Inhalator comprising:

a. controller unit having a first housing, a controller accommodated in the first housing, and a socket electrically connected to the controller; and b. an aerosol generator unit having an aerosol generator configured to generate an aerosol by nebulizing a fluid and accommodated in a second housing, and a plug electrically connected with the aerosol generator and configured to directly mate with and electrically connect to the socket, wherein the socket comprises a circuit board having two opposite sides, each side comprising a conductive path for electrical connection to electrical contacts of the plug.

2. Inhalator according to claim 1, wherein the socket or the plug is configured to detachably receive the plug or the socket in at least two different orientations for electrical connection between the plug and the socket.

3. Inhalator according to claim 1, wherein the plug comprises the electrical contacts extending into a chamber and being flexible in opposite directions, wherein the contacts are configured to respectively electrically connect with the conductive paths on the opposite sides of the circuit board of the socket, when the circuit board inserts between the electrical contacts.

4. Inhalator according to claim 1, wherein the first housing has a base for supporting the first housing on a horizontal surface, wherein the socket is located closer to the base of the first housing than to a top of the first housing as seen in a vertical direction, when the base is supported on the horizontal surface.

5. Inhalator according to claim 1, wherein the second housing has a bottom and a top, wherein the plug of the aerosol generator is located closer to the top than to the bottom, when the inhalator is in use.

6. Inhalator according to claim 1, wherein the controller comprises a circuit board, the socket being connected to one of the opposite sides of the circuit board and a power supply being connected to the other of the opposite sides of the circuit board each by an elastic contact/contact area connection and/or a plug/socket connection.

7. Inhalator according to claim 1, wherein the first and second housing being detachably connected by a latch, the latch comprising a lug integral with and extending from one of the first and second housing, the lug having a hole engaged with a protrusion integral with the other of the first and second housing and a flexible area extending a certain distance in a direction away from the connection to one of the first and second housing towards the hole, so as to enable flexure of the lug in the flexible area relative to the one of the first and second housing, whereby the lug is disengageable from the protrusion.

8. Inhalator according to claim 7, wherein the lug remains flexed after disengagement from the protrusion and is again engageable with the protrusion by flexure of the lug in the flexible area relative to the one of the first and second housings.

9. Inhalator according to claim 1, wherein a portion of the first housing accommodating at least a portion of the controller forms a handle so that the inhalator may be held during inhalation with a base of the first housing facing downward.

10. Inhalator according to claim 1, wherein the first housing and particularly a portion accommodating at least a portion of the controller form a grip for holding the inhalator during inhalation by one hand only.

11. Inhalator according to claim 1, wherein an opening in the second housing serves as vent during inhalation, wherein air is drawn in through the opening into a mixing chamber on its way to an outlet.

12. Inhalator according to claim 11, wherein a one-way valve is disposed in the opening so as to allow a flow of air from the outside to the inside only.

13. Inhalator according to claim 1, wherein the aerosol generator has a vibratable membrane with a plurality of apertures through which the fluid is passed for nebulization and a portion of the first housing accommodating at least a portion of the controller is arranged further away from a base of the first housing than the membrane as seen in the vertical direction, when the base is supported on the horizontal surface.

14. Inhalator according to claim 13, wherein the membrane is oriented substantially parallel to the base of the first housing.

15. Inhalator according to claim 1, wherein the aerosol generator is gravity fed in that the fluid is flown to the aerosol generator primarily by gravitational force.

16. Inhalator according to claim 1, wherein a fluid container containing the fluid to be nebulized is arranged on an opposite side of the aerosol generator relative to a base of the first housing and a portion of the first housing accommodating at least a portion of the controller is arranged further away from the base of the first housing than the fluid container as seen in the vertical direction, when the base is supported on the horizontal surface.

17. Inhalator according to claim 1, wherein the center of gravity of the inhalator is closer to a base of the first housing than to a top at an opposite side and furthest away from the base.

18. Inhalator according to claim 17, wherein the inhalator has a height defined in the vertical direction between the base and the top and the center of gravity is located in the lower third of the height.

19. Inhalator according to claim 18, wherein the center of gravity is located in the lower quarter of the height.

20. Inhalator according to claim 1, further comprising an outlet for delivery of the nebulized fluid to a patient, the outlet being located closer to a base of the first housing than the aerosol generator and a portion of the first housing accommodating at least a portion of the controller.

21. Inhalator set comprising:
an inhalator comprising:
  a controller unit having a first housing, a controller accommodated in the first housing, and a socket electrically connected to the controller; and
  an aerosol generator unit having an aerosol generator configured to generate an aerosol by nebulizing a fluid and accommodated in a second housing, and a plug electrically connected with the aerosol generator and configured to directly mate with and electrically connect to the socket, wherein the plug being part of the aerosol generator unit is electrically connectable to the socket in a first orientation; and
a cleaning unit configured to clean the aerosol generator, the cleaning unit having a third housing with a receiving section for receiving the aerosol generator and an opening for giving access to the plug of the received aerosol generator, so that the plug being part of the cleaning unit is electrically connectable to the socket in a second orientation different from the first orientation.

* * * * *